United States Patent
Sowa et al.

(10) Patent No.: US 12,328,516 B2
(45) Date of Patent: Jun. 10, 2025

(54) HYBRID VISIBLE AND NEAR INFRARED IMAGING WITH AN RGB COLOR FILTER ARRAY SENSOR

(71) Applicant: Kent Imaging Inc., Calgary (CA)

(72) Inventors: Michael Sowa, Calgary (CA); Matt Cervi, Calgary (CA)

(73) Assignee: Kent Imaging Inc., Calgary (CA)

( * ) Notice: Subject to any disclaimer, the term of this patent is extended or adjusted under 35 U.S.C. 154(b) by 0 days.

(21) Appl. No.: 18/771,596

(22) Filed: Jul. 12, 2024

(65) Prior Publication Data

US 2024/0365015 A1 Oct. 31, 2024

Related U.S. Application Data

(63) Continuation of application No. 16/616,722, filed as application No. PCT/CA2018/051128 on Sep. 12, 2018, now Pat. No. 12,069,383.

(Continued)

(51) Int. Cl.
*H04N 25/131* (2023.01)
*A61B 5/026* (2006.01)
(Continued)

(52) U.S. Cl.
CPC ......... *H04N 25/131* (2023.01); *A61B 5/0261* (2013.01); *H04N 23/11* (2023.01);
(Continued)

(58) Field of Classification Search
None
See application file for complete search history.

(56) References Cited

U.S. PATENT DOCUMENTS

| 5,777,674 A | 7/1998 | Ohmuro |
| 6,456,793 B1 | 9/2002 | Ray et al. |

(Continued)

FOREIGN PATENT DOCUMENTS

| EP | 2977003 A1 | 1/2016 |
| EP | 2362179 B1 | 8/2016 |

(Continued)

OTHER PUBLICATIONS

Altmann, Y., et al. Nonlinear Spectral Unmixing of Hyperspectral Images Using Gaussian Processes, IEEE Transactions on Signal Processing, 61(10): 2442-2453 (2013).

(Continued)

*Primary Examiner* — David N Werner
(74) *Attorney, Agent, or Firm* — Goodwin Procter LLP

(57) ABSTRACT

Near infrared imaging is highly complementary to color imaging having a wide range of applications. For example, in health applications, the near infrared can provide biomolecular information on tissue that is not apparent under visual examination nor from the inspection of color images of tissue. Thus, there is utility in viewing both visible color and near infrared images in combination. Described herein are methods to perform visible and near infrared imaging as well as hybrid visible color and near infrared imaging with a single conventional color filter array RGB sensor. The methods automatically provide spatially co-registered color and near infrared images and the methods can be used as the basis for a multispectral or hyperspectral imaging system.

22 Claims, 8 Drawing Sheets

Related U.S. Application Data

(60) Provisional application No. 62/558,949, filed on Sep. 15, 2017.

(51) Int. Cl.

| | | |
|---|---|---|
| *H04N 23/11* | (2023.01) | |
| *H04N 23/84* | (2023.01) | |
| *H04N 25/11* | (2023.01) | |
| *H04N 25/133* | (2023.01) | |
| *A61B 5/145* | (2006.01) | |
| *A61B 5/1455* | (2006.01) | |

(52) U.S. Cl.
CPC ............ *H04N 23/84* (2023.01); *H04N 25/11* (2023.01); *H04N 25/133* (2023.01); *A61B 5/145* (2013.01); *A61B 5/1455* (2013.01); *H04N 2209/047* (2013.01)

(56) References Cited

U.S. PATENT DOCUMENTS

| | | | |
|---|---|---|---|
| 6,734,962 B2 | 5/2004 | Treado et al. | |
| 7,012,643 B2 | 3/2006 | Frame | |
| 2002/0065468 A1 | 5/2002 | Utzinger et al. | |
| 2003/0020728 A1* | 1/2003 | Saquib | H04N 23/843 348/E9.01 |
| 2004/0225222 A1 | 11/2004 | Zeng et al. | |
| 2005/0276475 A1* | 12/2005 | Sawada | G06T 5/70 348/E3.018 |
| 2006/0008866 A1 | 1/2006 | Flick et al. | |
| 2007/0145273 A1* | 6/2007 | Chang | H04N 25/131 348/E9.003 |
| 2007/0201738 A1* | 8/2007 | Toda | H04N 25/133 382/144 |
| 2008/0079806 A1 | 4/2008 | Inuiya et al. | |
| 2008/0079807 A1 | 4/2008 | Inuiya et al. | |
| 2009/0159799 A1 | 6/2009 | Copeland et al. | |
| 2009/0318908 A1 | 12/2009 | Van Pieterson et al. | |
| 2010/0232692 A1* | 9/2010 | Kumar | H04N 23/843 348/208.4 |
| 2010/0262017 A1 | 10/2010 | Frangioni | |
| 2011/0063427 A1 | 3/2011 | Fengler et al. | |
| 2011/0080487 A1 | 4/2011 | Venkataraman et al. | |
| 2011/0117025 A1 | 5/2011 | Dacosta et al. | |
| 2011/0270092 A1 | 11/2011 | Kang et al. | |
| 2011/0301441 A1 | 12/2011 | Bandic et al. | |
| 2012/0078075 A1 | 3/2012 | Maynard et al. | |
| 2012/0200734 A1* | 8/2012 | Tang | H04N 25/131 348/E9.051 |
| 2012/0212619 A1 | 8/2012 | Nagamune | |
| 2013/0201342 A1 | 8/2013 | Skaff et al. | |
| 2013/0329101 A1 | 12/2013 | Choi et al. | |
| 2014/0152838 A1 | 6/2014 | Lee et al. | |
| 2014/0160253 A1 | 6/2014 | Backman et al. | |
| 2014/0257113 A1 | 9/2014 | Panasyuk et al. | |
| 2014/0267672 A1 | 9/2014 | Morrison et al. | |
| 2014/0320707 A1 | 10/2014 | Olson | |
| 2014/0333764 A1 | 11/2014 | Venkataraman et al. | |
| 2014/0355870 A1 | 12/2014 | Venkataraman et al. | |
| 2015/0173793 A1* | 6/2015 | Flint | A61B 17/3423 600/201 |
| 2015/0237321 A1 | 8/2015 | Sekiguchi et al. | |
| 2015/0287191 A1 | 10/2015 | Koruga et al. | |
| 2015/0288950 A1 | 10/2015 | Zhang | |
| 2015/0381909 A1 | 12/2015 | Butte et al. | |
| 2016/0022181 A1 | 1/2016 | Valsan et al. | |
| 2016/0069743 A1 | 3/2016 | McQuilkin et al. | |
| 2016/0117800 A1 | 4/2016 | Korkin | |
| 2016/0295135 A1 | 10/2016 | Sekiguchi et al. | |
| 2016/0330385 A1 | 11/2016 | Sekiguchi et al. | |
| 2016/0330386 A1 | 11/2016 | Sasao et al. | |
| 2017/0064222 A1 | 3/2017 | Nakamura | |
| 2017/0064275 A1 | 3/2017 | Chen et al. | |
| 2017/0127988 A1 | 5/2017 | Tao et al. | |
| 2017/0186133 A1* | 6/2017 | Kunze | H04N 25/131 |
| 2017/0223316 A1 | 8/2017 | Zeng et al. | |
| 2017/0258330 A1 | 9/2017 | Tsumatori | |
| 2017/0272709 A1 | 9/2017 | Hagiwara et al. | |
| 2018/0041714 A1* | 2/2018 | Hayashi | G06T 5/73 |
| 2018/0047185 A1* | 2/2018 | Boisson | H04N 23/80 |
| 2018/0146144 A1* | 5/2018 | Sugiyama | H04N 23/20 |
| 2018/0262725 A1 | 9/2018 | Fan | |
| 2018/0359432 A1* | 12/2018 | Horak | H04N 23/11 |
| 2019/0187048 A1 | 6/2019 | Wood et al. | |
| 2019/0361252 A1 | 11/2019 | Nagae | |
| 2020/0330028 A1 | 10/2020 | Nejati | |
| 2021/0075978 A1 | 3/2021 | Sowa et al. | |

FOREIGN PATENT DOCUMENTS

| | | |
|---|---|---|
| JP | 2008527544 A | 7/2008 |
| WO | WO-2017112753 A1 | 6/2017 |

OTHER PUBLICATIONS

Attas, M., et al., Visualization of cutaneous hemoglobin oxygenation and skin hydration using near-infrared spectroscopic imaging, Skin Res Technol, 7(4): 238-245 (2001).

Beck, A., et al., A fast iterative shrinkage-thresholding algorithm for linear inverse problems, SIAM J Imaging Sciences, 2(1): 183-202 (2009).

Bruckstein, A.M., et al., On the uniqueness of nonnegative sparse solutions to underdetermined systems of equations, IEEE Transactions on Information Theory, 54(11), pp. 1-23 (2008).

Chandrasekaran, V., et al., The convex geometry of linear inverse problems, Found Comput Math, 12: 805-849 (2012).

Chen, D., et al., Nonnegativity constraints in numerical analysis, Birth of Numerical Analysis, pp. 109-139 (2009).

Chen, S-J., et al., Multispectral Image Out-of-Focus Deblurring Using Interchannel Correlation, IEEE Trans Image Process, 24(11): 4433-4445 (2015).

Choi, Y.-J., et al., Cell analysis system using a filter-free fluorescence sensor, 2017 19th International Conference on Solid-State Sensors, Actuators and Microsystems (Transducers), Kaohsiung, Taiwan, pp. 198-201 (2017).

Cotter, S.F., et al., Sparse solutions to linear inverse problems with multiple measurement vectors, IEEE Transactions on Signal Processing, 53(7): 2477-2488 (2005).

De Decker, B., et al. Capturing multiple illumination conditions using time and color multiplexing, IEEE Conference on Computer Vision and Pattern Recognition, pp. 2536-2543 (2009).

Dobigeon, N., et al., Nonlinear unmixing of hyperspectral images: Models and algorithims, IEEE Signal Processing Magazine, 31(1): 82-94 (2014).

Donoho, D.L., et al., Sparse nonnegative solution of underdetermined linear equations by linear programming, Prov Natl Acad Sci USA, 102(27): 9446-9451 (2005).

EP 18855361.4 94(3) Communication dated Jan. 4, 2024.

Heylen, R., et al., A review of nonlinear hyperspectral unmixing methods, IEEE Journal of Selected Topics in Applied Earth Observations and Remote Sensing, 7(6): 1844-1868 (2014).

Iordache, M-D., et al., Total variation spatial regularization for sparse hyperspectral unmixing, IEEE Transactions on Geoscience and Remote Sensing, 50(11): 4484-4502 (2012).

Lapray, P-J., et al., Multispectral filter arrays: recent advances and practical implementation, Sensors (Basel), 14(11):21626-21659 (2014).

Lukac, R., et al., Color filter arrays: Design and performance analysis, IEEE Transactions on Consumer Electronics, 51(4): 1260-1267 (2005).

Morris, H.R., et al., Imaging Spectrometers for Fluorescence and Raman Microscopy: Acousto-Optic and Liquid Crystal Tunable Filters, Society for Applied Spectroscopy, 48(7): 857-866 (1994).

Nakazawa, H., et al., A filter—less multi-wavelength fluorescence detector, 2011 16th International Solid-State Sensors, Actuators and Microsystems Conference, Beijing, China, pp. 100-103 (2011).

(56) References Cited

OTHER PUBLICATIONS

Pu, H., et al., Constrained Least Squares Algorithms for Nonlinear Unmixing of Hyperspectral Imagery, IEEE Transactions on Geoscience and Remote Sensing, 53(3): 1287-1303 (2015).

Salehani, Y.E., et al., $\ell_0$-Norm Sparse Hyperspectral Unmixing Using Arctan Smoothing, Remote Sens, 8(3): 187, pp. 1-20 (2016).

Seo, I., et al., Assessing human skin with diffuse reflectance spectroscopy and colorimetry, Progress in Biomedical Optics and Imaging—Proceedings of SPIE, 8207: pp. 1-5 (2012).

Sowa, M., et al., Detecting Intestinal Ischemia Using near Infrared Spectroscopy, J Near Infrared Spectrosc, 14: pp. 1-7 (2006).

Sowa, M., et al., The Utility of near Infrared Imaging in Intra-Operative Prediction of Flap Outcome: A Reverse McFarlane Skin Flap Model Study, J Near Infrared Spectrosc, 20(5): 601-615 (2012).

Sowa, M.G., et al., Classification of burn injuries using near-infrared spectroscopy, J Biomed Opt, 11(5): 054002 (2006).

Sowa, M.G., et al., Review of near-infrared methods for wound assessment, J Biomed Opt, 21(9): 091304 (2016).

Tanaka, K., et al., Realization of filter-free fluorescence image sensor, 2017 19th International Conference on Solid-State Sensors, Actuators and Microsystems (Transducers), Kaohsiung, Taiwan, pp. 1616-1619 (2017).

Tropp, J.A., et al., Computational Methods for Sparse Solution of Linear Inverse Problems, Proceedings of the IEEE, 98(6): 948-958 (2010).

Tsumura, N., et al., Regression-based model of skin diffuse reflectance for skin color analysis, Optical Review, 15: 292-294 (2008).

Tuia, D., et al., Nonconvex Regularization in Remote Sensing, IEEE Transactions on Geoscience and Remote Sensing, 54 (11): pp. 1-12 (2016).

Wang, M., et al., A Unique "Nonnegative" Solution to an Underdetermined System: From Vectors to Matrices, IEEE Transactions on Signal Processing, 59(3): 1007-1016 (2011).

Widdowson, D.C., et al., Construction of a novel port wine stain phantom and measurement of colour by digital imaging and reflectance spectrophotometry, Lasers Med Sci, 23(4): 369-374 (2008).

Xiang, X., et al., An Update on Novel Non-Invasive Approaches for Periodontal Diagnosis, Journal of Periodontology, 81(2): 186-198 (2010).

Yuan, Q., et al., Hyperspectral Image Denoising Employing a Spectral-Spatial Adaptive Total Variation Model, IEEE Transactions on Geoscience and Remote Sensing, 50(10): 3660-3677 (2012).

\* cited by examiner

HYBRID VISIBLE AND NEAR INFRARED IMAGING WITH AN RGB COLOR FILTER ARRAY SENSOR

CROSS-REFERENCE

This application is a continuation of U.S. application Ser. No. 16/616,722, filed Nov. 25, 2019, now issued as U.S. Pat. No. 12,069,383 on Aug. 20, 2024, which is the National Stage entry of International Application No. PCT/CA2018/051128, filed Sep. 12, 2018, which claims the benefit of U.S. Provisional Application No. 62/558,949, filed Sep. 15, 2017, the contents of each of which are herein incorporated by reference in their entireties.

BACKGROUND OF THE INVENTION

Near infrared imaging, alone or in combination with colour imaging, has a wide range of applications spanning many disciplines. For example, it is used extensively in remote sensing and satellite imaging. By collecting the sunlight reflected by the earth over several wavelength regions (multispectral) or very many wavelength regions (hyperspectral), chemical and biochemical information can be obtained. Crop health can be assessed by analysing the reflected multi/hyper spectral signature from vegetation. Pollutants can be detected, localized and characterized by their spectral signatures from the analysis of multi/hyperspectral images.

Near infrared imaging, as a remote sensing methodology, has far ranging utility in ecology, agriculture and geology. While less established, the remote sensing capabilities of near infrared imaging can be exploited in medicine. Again, different chemical/biochemical species can be detected, localized and monitored over time remotely and non-invasively, without the need for taking a tissue sample. Near infrared is non-ionizing radiation lower in energy than visible light and thus can be used safely in much the same way as we use visible light to safely visualize tissue. Fiber optics are also well able to transmit near infrared light which enable near infrared light to be used in endoscopic type of applications.

In this disclosure, we are particularly concerned with medical imaging as well as applications in personal aesthetics, health and wellness. The near infrared region of the electromagnetic spectrum can provide biomolecular information on tissue that is not apparent under visual examination nor from the inspection of colour images of the tissue. [1-6] For example, tissue water content can be visualized using near infrared imaging. Tissue water content or hydration is an important indicator of tissue health. In highly inflamed tissue, excessive water content (edema) can be detrimental while fluid management, particularly in burn wounds, is an important factor in patient outcome. Near infrared spectroscopic analysis can determine when edema becomes a problem and also determine the fluid balance of burn patients. There are also regions of the near infrared electromagnetic spectrum that can be used to provide information that corroborates features that can be observed visually or from conventional colour imagery. For example, the reddish hue of skin is associated with the perfusion of well oxygenated blood. Blood oxygenation can also be measured by multi/hyperspectral near infrared imaging.

Owing to its complementarity to visual assessment, there are compelling reasons to pursue the near infrared imaging of tissue. Visual assessment still plays an important role in clinical diagnosis and in order to maximize the utility of near infrared imaging, there is merit in providing both color imagery and near infrared imaging in combination. Projecting or displaying near infrared images of tissue within a visually recognizable anatomical context provides such a capability. One of the simplest ways to achieve this context is to have a conventional colour image of the tissue that is matched to the near infrared image. Performing near infrared imaging in conjunction with visible imaging where the two information streams are spatially matched is particularly powerful.

Previous solutions to this problem required multiple sensors. Those solutions were used in combination with splitting or further filtering the incoming light which added further cost and complexity to the imaging system. FIG. 1 a shows a typical two sensor solution where one sensor is a standard digital colour camera sensor and the second sensor is used to capture the multi/hyperspectral image.

Single sensor solutions tend to lead to simpler, often more efficient and usually more cost-effective means to address this problem. One such single sensor solution combines visible and near infrared color filter arrays to provide combined visible—near infrared imaging. [7] These arrays are not common and can be very expensive. In addition, as the number of color filters are increased to provide for more multispectral channels the effective spatial resolution of the sensor decreases. Thus, as an imaging solution, this solution trades off spatial versus spectral information making it most useful when only a small number of multispectral imaging channels (wavelength regions) are needed.

Other single sensor solutions sequentially image a scene accepting a limited but varying spectral bandpass of light at each image within the sequence. [8] This latter solution and to some extent the multiple sensor solution is challenged to ensure spatial alignment between the color image or visible light images and the near infrared images. Depending on the wavelength switching and selection process such a solution can be costly. Often further processing of the images is required to ensure that they are spatially matched (registered). FIGS. 1b and 1c diagram two popular sequential scanning configurations. In the first single sensor solution a mechanical or electronic filter is used to sequentially pass a varying spectral bandpass to the imaging sensor. The electro-mechanical filter adds complexity to this design. In FIG. 1c a series of illuminants with different spectral emission characteristic sequentially illuminate the target sample. This latter design eliminates the electro-mechanical filter relying instead on the series of illuminants to enable multi/hyperspectral imaging.

In this disclosure, we propose a solution that borrows from the configuration outlined in FIG. 1c but that overcomes many of the challenges with less complexity compared to previous hybrid visible-near infrared imaging approaches.

SUMMARY OF THE INVENTION

Described herein is a method is provided that uses conventional color filter array (CFA) color imaging sensors to perform visible-near infrared (350-1100 nm) multispectral/hyperspectral imaging. CFA RGB color imaging sensors are the key component in most commercial digital cameras including those in our cellular phones. We can leverage this ubiquitous technology in our embodiment, however our method is equally applicable to custom multichannel light sensors. Our method requires no splitting, dividing or attenuation of the input light nor are additional or specialized optical components needed in the optical light path. The resultant color and near infrared images are automatically spatially aligned. The color and near infrared image captured simultaneously can be acquired in a single-shot (frame) of the sensor as well as using a sequence of frames to improve performance and provide for a more robust color and visible-near infrared multispectral or hyperspectral imaging capacity.

The method relies on using one or more sources or illuminants that result in light output that can be varied using techniques such as multiplex encoding or modulation or be spectrally distinct with respect to the CFA of the sensor. The latter approach will be further described. The illuminants used span the spectral regions of interest which are dictated by the imaging application. The imaging target reflects some of the light of the illuminants which in turn is detected by the color sensor. The multichannel signal from the color sensor can be unmixed/decomposed to provide the spectral contributions from the individual sources/illuminants. Given that these illuminants span the spectral regions of interest, the unmixed/decomposed signal effectively enables the performance of multispectral/hyperspectral imaging. In some circumstances, such as when the number of sources/illuminants is less than the number of sensor channels or the number of image frames captured approaches the number of illuminants, the unmixing/decomposition process is a well-posed problem and standard methods can be used to recover the source signals. For example, the least squares solution to the linear unmixing model provides for a reliable recovery of the spectral imaging information. However, in the most general application of this method the unmixing or spectral recovery problem is ill-posed yielding an infinite number of possible solutions to the inverse problem. Using physical and practical constraints imposed by the imaging configuration and the optical properties of the target, as disclosed herein, and/or a constrained set or dictionary of spectral targets the solution space can be narrowed to often give a useful recovery of the source/illuminant signals.

DESCRIPTION OF THE PREFERRED EMBODIMENTS

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

Described herein is a method to perform near infrared and visible light colour imaging with one color filter array (CFA) RGB sensor. Conventional commercial CFA RGB sensors [7, 9] can be used. The method requires no splitting, dividing or attenuation of the input light nor are additional or specialized optical components needed in the optical light path. The resultant color and near infrared images are automatically spatially aligned. The color and near infrared image captured simultaneously can be acquired in a single-shot or frame of the sensor or by using a sequence of frames to improve performance and provide for a more robust color and visible-near infrared multispectral or hyperspectral imaging capacity.

Figure 1A:
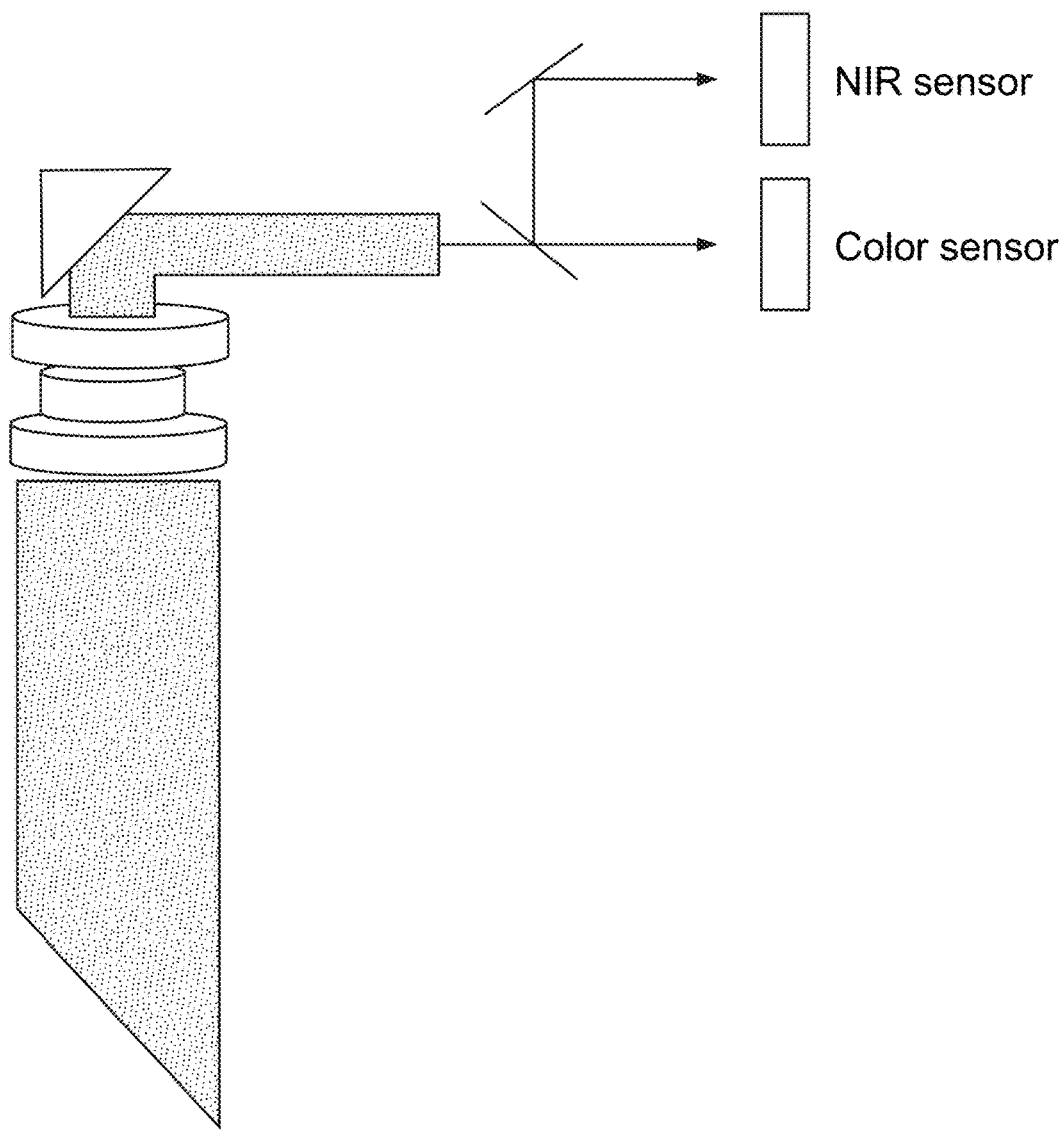
FIG. 1a: Prior art hybrid visible (color) and near infrared reflectance imaging configuration using a separate imaging sensor for the color imaging and the near infrared (NIR) imaging. This conventional configuration requires that the reflected light is split between the two sensors. The splitting optics attenuates the light impinging on the sensors as well as introduces design and cost complexities, as well as unwanted optical aberrations.
Figures 1B, 1C:
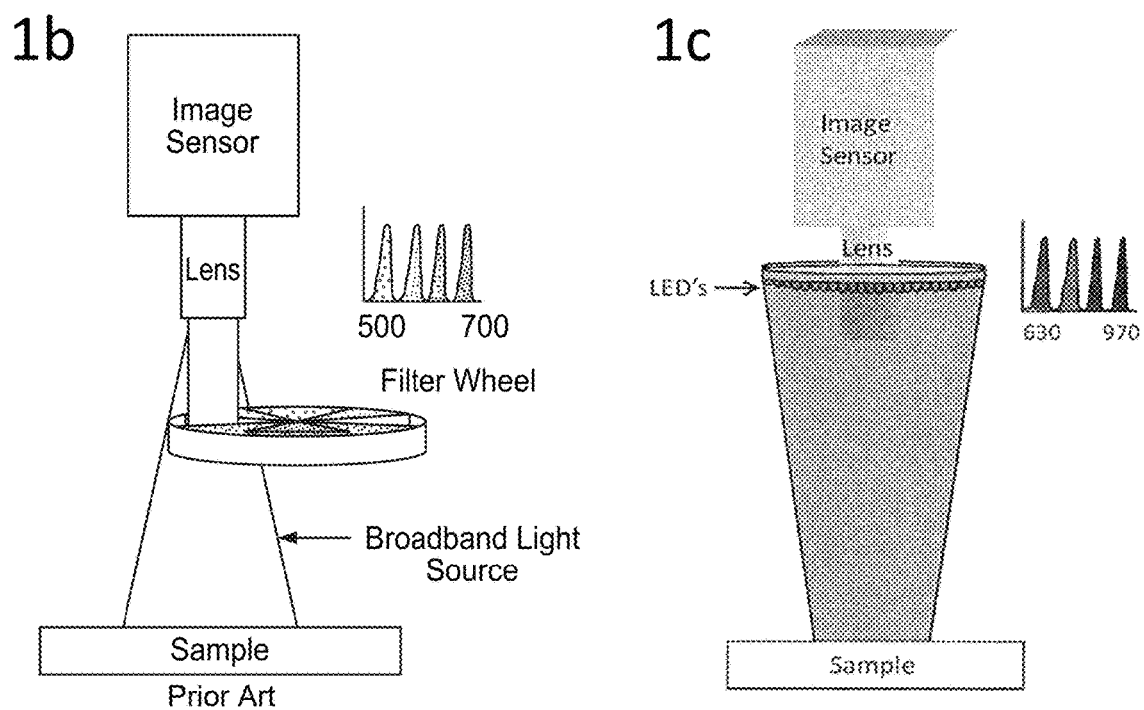
FIG. 1b: Prior art hybrid visible (color) and near infrared reflectance imaging configuration using a single imaging sensor that relies on a mechanical or electronic optical filter to sequentially select a bandpass of spectrally distinct light reflected from the target sample being illuminated by a spectrally broad light source.
FIG. 1c: hybrid visible (color) and near infrared reflectance imaging configuration using a single imaging sensor that relies on a series of spectrally distinct illuminants to sequentially illuminate the target sample.
Figure 2:
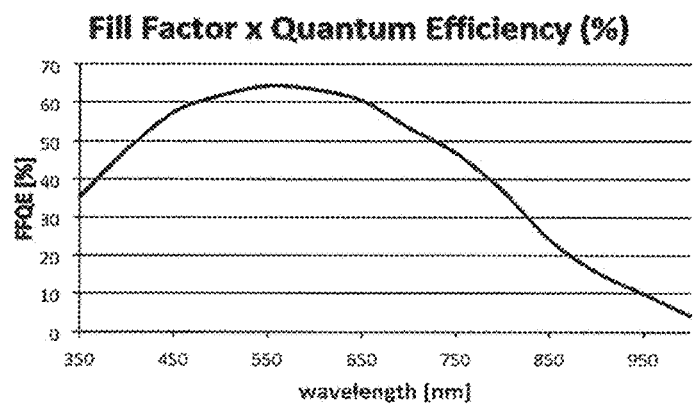
FIG. 2: Typical spectral response of a CMOS/CCD imaging sensor. These sensors are intrinsically sensitive to both visible and short wavelength near infrared light.

FIG. 2 shows the spectral response of a typical CMOS sensor. CMOS sensors have intrinsic sensitivity to near infrared light. In most color camera designs a color filter array (CFA) is placed in front of the sensor in a Bayer pattern. In FIG. 3 a schematic of the Bayer filter pattern is provided along with the spectral responsivity of the red (R), green (G) and blue (B) channels of a CF A-CMOS sensor. Generally, CFA-CMOS sensors retain their sensitivity to near infrared light. The R, G and B channels in a typical CFA-CMOS sensor differ in their near infrared response. We demonstrate how these sensors can be used for visible-near infrared imaging. A response for each pixel from a CFA sensor is usually modelled by Equation (1).

$$y_k = \int_{min(\lambda)}^{max(\lambda)} l(\lambda)\xi(\lambda)f_k(\lambda)r(\lambda) \tag{1a.}$$

The output of the $k^{th}$ filter, $y_k$, is given by the integral over the minimum to maximum wavelengths, $\lambda$, of the sensor of the product of the spectral radiance of the illuminant, $l(\lambda)$, the spectral sensitivity of the sensor, $\xi(\lambda)$, the spectral transmittance of the $k^{th}$ filter, $f_k(\lambda)$ and the spectral reflectance of the scene, $r(\lambda)$. Note that the descriptions and equations that follow can apply to spatially resolving sensors which output information as pixelated images or area or volume resolving measurements. For conciseness and clarity, we have dropped the spatial, area or volume labels in our description of the preferred embodiments. However, the formulations given below also apply to spatially resolving sensors or sensing schemes.

Figure 3A:
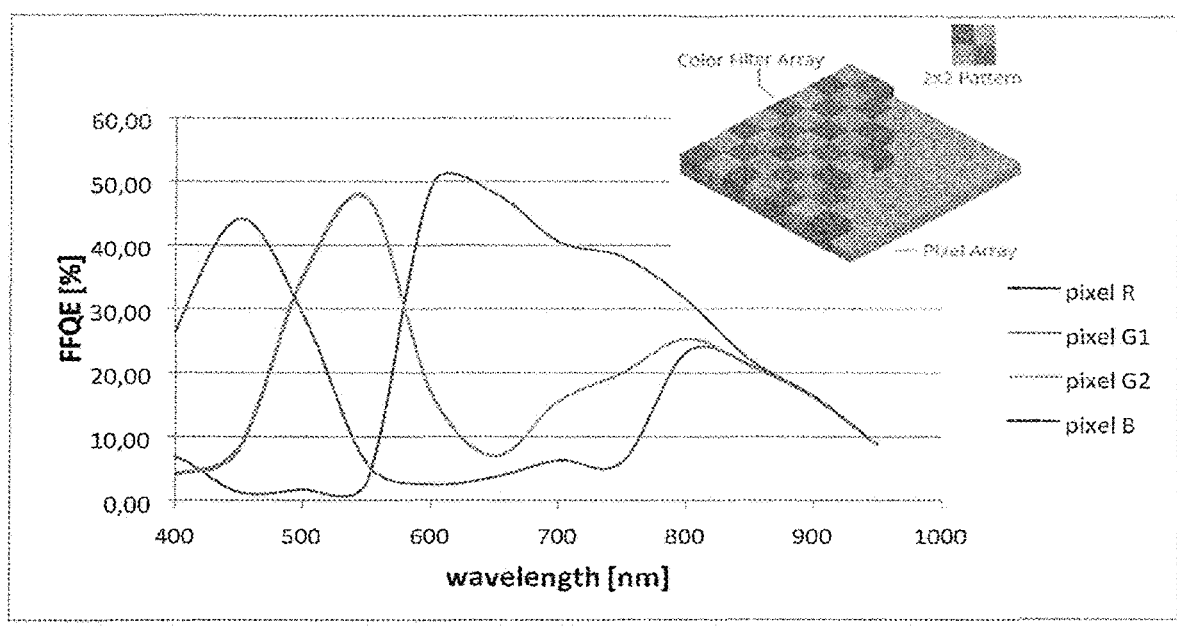
FIG. 3a: Typical spectral response of a RGB color filter array (CFA) CMOS imaging sensor. The red, green and blue pixels generally have responsivity to near infrared light. This responsivity is usually blocked by imposing an infrared cut-off filter in front of the CFA. Without a blocking filter the R, G and B channels show a different responsivity to near infrared light. This responsivity can be exploited to give the RGB sensor near infrared imaging capability.
Figure 3B:
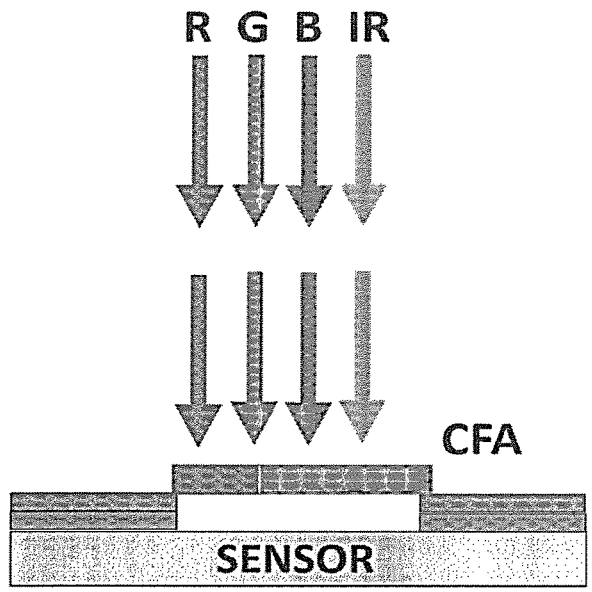
FIG. 3b: Schematic depiction of a red-green-blue (RGB) color image sensor employing a color filter array (CFA) mask in front of an array image sensor thereby providing subsets of pixels sensitive to red, green or blue light. In most RGB sensors an infrared filter is employed to block infrared light from impinging on the imaging sensor. Our methods require that the infrared blocking filter is removed or that the sensor does not employ such a blocking filter.

The conventional CFA sensor consists of four filters, one filter weighted to transmitting red colours, one largely transmitting blue colours and two green transmitting filters, see FIG. 3a. The embodiments of the invention described herein do not preclude the use of multiple sensors or a different number of set of filters. However, in our examples, we use a single sensor with a known spectral sensitivity and known spectral transmittance of the conventional R-G-G-B CFA filter design to perform visible-near infrared spectral imaging (FIG. 3b). We define the effective sensitivity of the sensor for each filter channel as, $\xi_k^{eff}=\xi f_k$ leading to expression 1b, $$y_k = \int_{min(\lambda)}^{max(\lambda)} l(\lambda)\xi_k^{eff}(\lambda)r(\lambda) \tag{1b.}$$

Defining $1_k^{eff}=I\xi_k^{eff}$ as the effective instrumental response to the illuminant, further simplifies equation (1a) to 1c, $$y_k = \int_{min(\lambda)}^{max(\lambda)} l_k^{eff}(\lambda)r(\lambda) \tag{1c.}$$

In matrix notation, (1c) can be written as, $$y = Lr \tag{1d}$$

where y is the output of the sensor, L is a representation of the multiplexing matrix and r is the reflectance of the scene. The general aim of multispectral or hyperspectral imaging is to determine the spectral reflectance of the scene, $r(\lambda)$, at various wavelengths or wavelength ranges by measuring $y_k$ from several filters, or using different illuminants or using multiple filters in combination with different illuminants. The formulation given by equation 1 considers reconstruction of the scene reflectance, r, from the sensor output, y, as a linear inverse problem.

$$\hat{r} = L^{-1}y \tag{2}$$

In some instances, nonlinear extensions of equation (1) are useful. [10-13] However, examples will consider the linear inverse problem and exploit the four filters of a conventional CFA-RGB sensor and various ways to combine illuminants to perform visible-near infrared imaging.

It may also be useful to model the spectral reflectance as combinations of a set of basis functions, members of a spectral library or from an imposed or learned dictionary. For example, the dictionary could contain known reflectance signatures of a plurality of substances, for example, substances expected to be examined or encountered when carrying out methods of the invention. In such instances, scene reflectance is generally modelled by equation (3) where $b_j$ represent some prototype function describing an aspect or constituent of the spectral reflectance of the scene and $a_j$ describes the magnitude of the contribution of the $j^{th}$ constituent to the overall reflectance. Often the coefficient vector a is referred to as the abundance vector.

Using equation (3) or related models to describe scene reflectance, multispectral or hyperspectral imaging reduces to recovering the constituents and their abundances ($a_j$) that account for the measured output of the sensor. Equation 1 then becomes, $$r(\lambda) = \sum_{j=1}^{N} b_j(\lambda)a_j \tag{3a}$$

$$r = Ba \tag{3b}$$

with LB replacing L.

For example, a dictionary may for example contain the known reflectance signature of 10 substances. When a reflectance measurement is taken at several wavelengths, the measured reflectance could be compared to the 10 reflectance signatures in the dictionary, wherein the closest match would identify the substance measured.

By extension if you are still limited to those 10 substances but there may be more than one in any given pixel of your image or you use more than one image taken at different wavelengths (multispectral image), you then need to "unmix" the reflectance measured at the separate wavelengths (wavelength regions) and get the abundance of each of those 10 substances at each pixel, for example by using equation 4 (above). If the reflectance signatures are reasonably different over the different wavelengths you are measuring then (4) can be solved robustly (usually using 10 or more wavelengths) to yield the abundances. With fewer wavelengths you need to applied prior knowledge about the system and any constraints associated with the system in order to solve Equation 4 and have the solutions give one a meaningful answer.

In the most general sense the problems related by equations (1) and (4) can be expressed as the reflectance information, x, from the scene being encoded by $\Phi_k$ to produce $y_k$, the sensor output from channel k.

$$y_k = \langle x, \phi_k \rangle \quad (5a)$$

Or in matrix-vector form as, $$y = \Phi x \quad (5b.)$$

where y output measurements from the sensor, $\Phi$ is an encoder matrix and x desired information on the reflectance of the scene. Our embodiments describe various means to usefully encode and decode CFA-RGB sensor output to provide hybrid visible-near infrared multispectral or hyperspectral imaging capacity.

Figure 4:
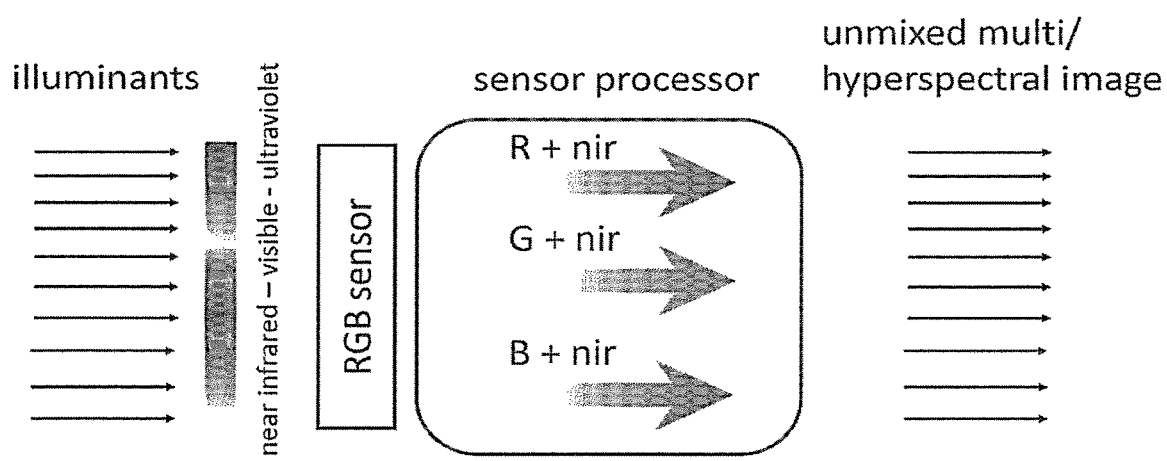
FIG. 4: Multi/hyperspectral imaging using spectrally diverse illuminants and a conventional CFA-RGB imaging sensor. The R+nir, G+nir and B+nir signals from a CFA-RGB sensor are unmixed/decomposed to recover the spectral information conveyed by the illuminants using one or more of the methods described herein to permit multi/hyperspectral imaging over the visible-near infrared region (350-1100 nm). When the CFA-RGB imaging sensor is used as a multichannel sensor, fewer imaging frames are needed to acquire a multi/hyperspectral image.

One embodiment of our method is summarized in FIG. 4. Therein, a scene is illuminated by one or more light sources or illuminants, within the visible-near infrared regions of the electromagnetic spectrum (350-1100 nm). Equation (6) describes a system with m light sources. Note that the illumination sources used in this embodiment could emit exclusively in the visible or the near infrared or both regions of the electromagnetic spectrum. These situations may arise when either visible or near infrared imaging may be required. As will be apparent to one of skill in the art, our invention is compatible with those situations as well as when both visible and near infrared imaging information is required.

$$l(\lambda) = \sum_{i=1}^{m} l_i(\lambda) \quad (6.)$$

The light reflected from the scene is captured by the system which reports the reflected light intensity separately for the R, G, G and B filtered pixels of CFA-sensor. The RGGB output channels of the sensor are processed to recover the contribution of the reflected light from each of the light sources or the reflectance of the scene over multiple wavelength regions as discussed herein.

For m distinct light sources and k output channels of the sensor, typically 4 for an RGGB Bayer CFA sensor, the encoding matrix describes the effective response of the separate channels of the sensor to each light source. In the simplest embodiment, one illuminant is used and the system is over-determined and only one sensor channel is needed to directly recover the contribution of light reflected from the single source. Thus in this example, the inverse of encoding matrix can be well approximated and equation 5 has a direct solution to recover the scene reflectance. To perform multispectral or hyperspectral imaging with this configuration, separate images with different illuminants need to be acquired. A simple practical example of using the above approach to collect an m frame multi/hyperspectral imaging would be to have m illuminants and collect a series of m images where each illuminant is flashed in sequence. This approach can be extended to flashing combinations of the m illuminants and collecting one frame for each different combination. Knowing the combination of illuminants and their relative intensities for each frame enables the user to "unmix" the combinations and recover the m frame multi/hyperspectral image. The latter procedure demonstrates that illuminant multiplexing is compatible with the described approach where effectively the R-G-G-B CFA sensor is used as a single channel sensor.

Figure 5A:
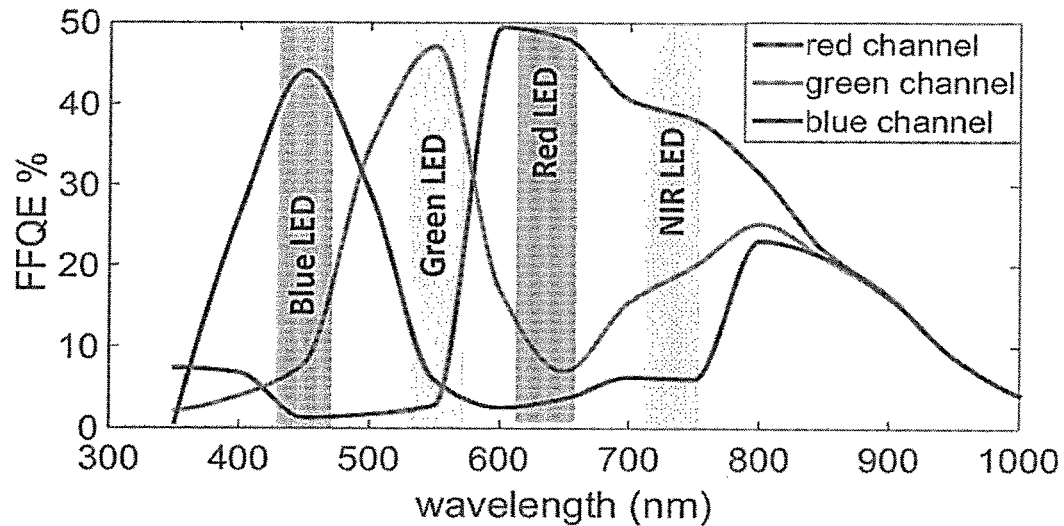
FIG. 5a: This example uses the CFA-RGB sensor as a 4 channel sensor in combination with 4 LEDs spanning the blue, green, red and near infrared responsivity of the sensor enabling 4 channel multispectral imaging using a single image frame from the sensor.
Figure 5B:
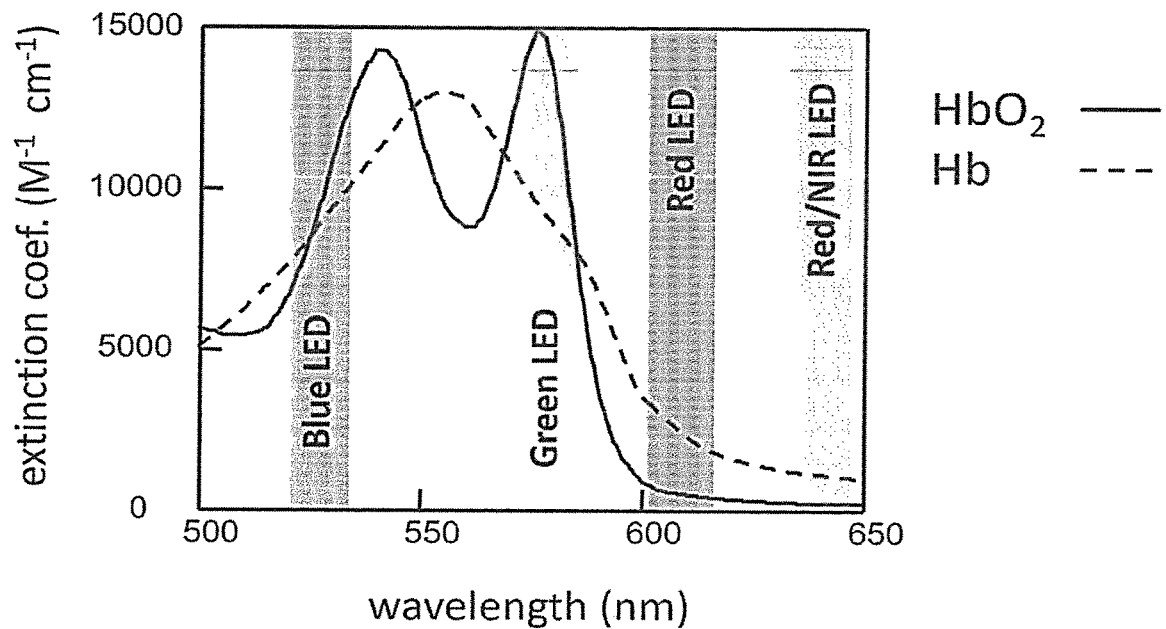
FIG. 5b: An example of hemoglobin oxygen saturation imaging is provided using the configuration outlined in FIG. 5a. The example uses 4 LEDS, a blue/green LED, green LED, red LED and deep red or near infrared LED in combination with a conventional CFA-RGB sensor to determine the proportion of oxygenated hemogloblin {hemoglobin oxygen saturation). When the CFA-RGB sensor is used as a four channel sensor this configuration can image hemoglobin oxygen saturation in a single image.
Figure 5C:
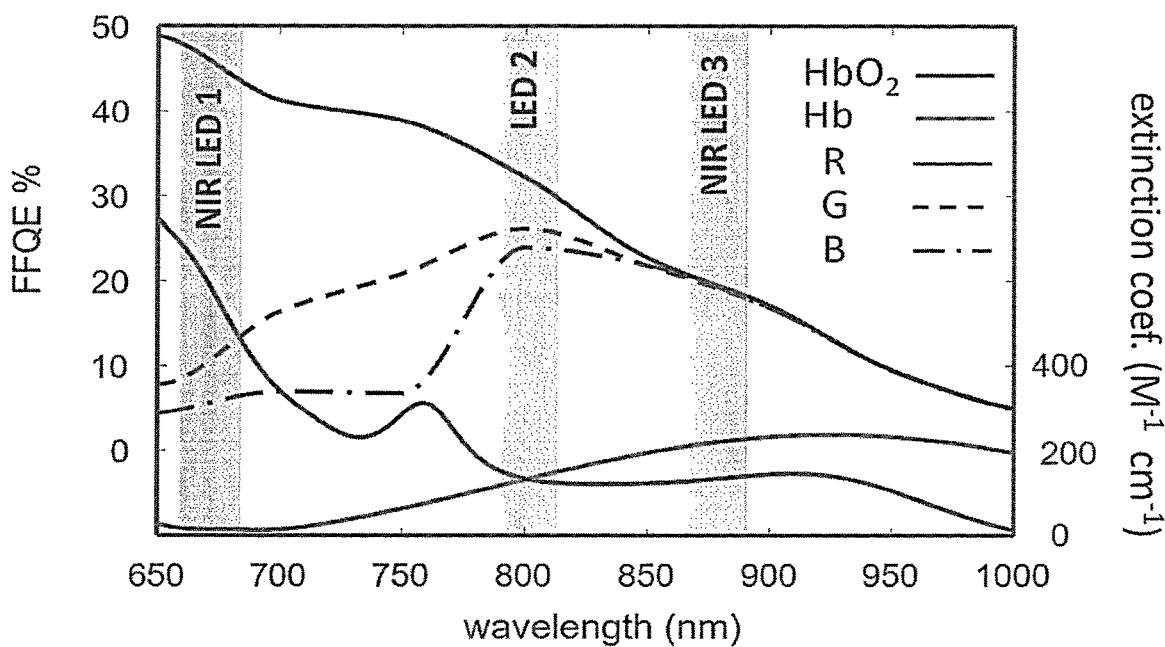
FIG. 5c: An example using 3 near infrared LEDs as illuminants in combination with a conventional CFA-RGB sensor to determine the proportion of oxygenated hemoglobin (hemoglobin oxygen saturation). When the CFA-RGB sensor is used as a three or four channel sensor in this configuration a near-infrared based hemoglobin oxygen saturation image can be acquired in a single frame from the sensor.
Figure 5D:
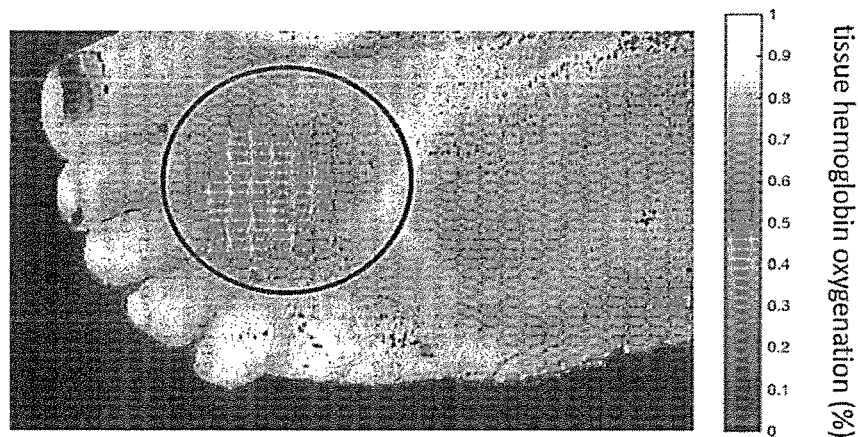
FIG. 5d: The resulting hemoglobin oxygen saturation image derived from a near infrared multispectral image acquired with a conventional CFA-RGB sensor used as a multichannel sensor. The circled area indicates a region of poor oxygenation in the area just before the three middle toes of the foot.
Figure 6:
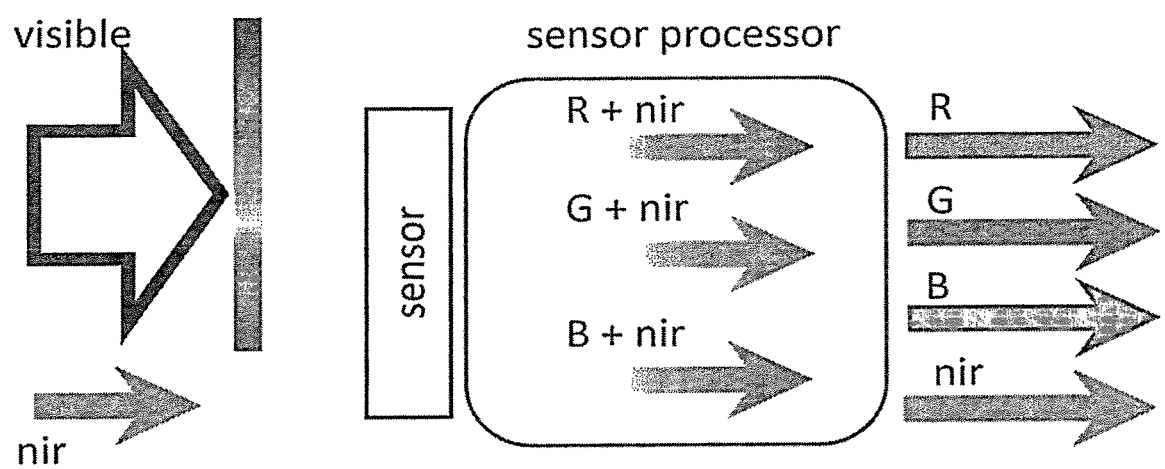
FIG. 6: A scene illuminated by a broadband visible light source and a nir light source is captured by a RGGB sensor. The R+nir, G+nir and B+nir signals from the sensor are unmixed using one or more of the methods described herein to provide R, G, B color and a nir signal.

As implied by equation (6) and as discussed herein, the CFA-RGB sensor can be used as a multichannel sensor. When used as a multichannel sensor and in combination with illuminants with different spectral profiles, m dimensional multi/hyperspectral imaging can be done with fewer than m image frames collected from the sensor. Under those circumstances, and if the inverse of the encoding matrix exists, the reflectance of the scene owing to each of the illuminants can be determined by equation (5). FIG. 5a highlights an example where illumination from 4 LEDs, 3 with visible light emission and one with near infrared emission, can be recovered from the RGGB output of a CFA-RGB sensor. FIG. 5b demonstrates how such a configuration could be used, for example, to provide a measure of hemoglobin oxygen saturation (the proportion of oxygenated hemoglobin) when the emitting wavelengths of the LEDs are selected to match the light absorbance of oxygen carrying hemoglobin and deoxygenated hemoglobin. In this example, the visible light absorbing characteristics of oxygenated and deoxygenated hemoglobin are used to provide a measure of hemoglobin oxygen saturation. Thus, in this example, a 4 channel multispectral imaging is collected by capturing a single imaging frame of the CFA sensor where the R-G-G-B outputs of the sensor are treated as separate signal channels and the illuminants are unmixed using the well conditioned inverse of the encoding matrix in equation 5. Furthermore, using a basis or dictionary type representation, equation 3, the constituent abundances can be estimated from the mathematical unmixing. By comparison if the RGB-CFA detector is used as a single channel sensor, four separate frames of the sensor would be needed to acquire the information necessary to determine the hemoglobin oxygen saturation. In some instances, it is also valuable to use the R-G-G-B sensor as a 2 or 3 channel sensor in combination with 2 or illuminants. These configurations can often lead to an improvement in the signal-to-noise ratio of the desired information. FIG. 5c demonstrates how 3 near infrared illuminants can be used to form a hemoglobin oxygen saturation image from a single frame of the R-G-G-B sensor acting as 3 or 4 channel sensor. In this example, the near infrared light absorption characteristics of oxygenated and deoxygenated hemoglobin are used to provide a measure of hemoglobin oxygen saturation. FIG. 5d shows a gray scale tissue hemoglobin oxygenation image derived from a near infrared multispectral image acquired using a conventional CFA-RGB sensor as a multichannel sensor. This arrangement can be used to rapidly and non-invasively detect areas of tissue with poor oxygenation. One of skill in the art can deduce variations of the examples presented in FIGS. 5b and 5c that jointly exploit the visible and near infrared optical properties of the target sample and enable hybrid visible-near infrared multispectral imaging. Similarly, as illustrated in FIG. 6, this method can be used to do color imaging in conjunction with near infrared imaging.

As the number of illuminant sources approaches and exceeds the number of sensor channels, m>k, the problem becomes increasingly under-determined and ill-posed. Assuming that equation 5 admits feasible solutions and therefore the encoding matrix is full rank, equation 5 has an infinite set of solutions when m>k. One particular solution is the least b norm solution using the pseudo-inverse of the encoding matrix, $$\bar{x} = \Phi^+ y \quad (7a)$$

where, $$\Phi^+ = \Phi^T(\Phi\Phi^T)^{-1} \quad (7b)$$

and T denotes the transpose operator. This can be expressed as the following optimization problem, $$\min\{\|x\|_2 \mid \Phi x = y, x \in \mathcal{R}^n\} \quad (7c.)$$

Often the minimum $l_2$ norm solution is a bad approximation to x and other minimum norm solutions are desirable.

$$\min\{\|x\|_p \mid \Phi x = y, x \in \mathcal{R}^n\} \quad (7d.)$$

Popular norms include p=0 and p=1 which tend to promote sparsity but solutions based on other norms or metrics can be used. However, the measurement of reflectance from an illuminated scene has some physical constraints and these constraints can be used to narrow the solution space for equation 5. Thus, the problem can be cast as a constrained optimization problem using a penalty function to measure the quality of the candidate solutions conforming to the imposed constraints.

$$\min\{\rho(x) \mid \Phi x = y, x \in \mathcal{R}^n\} \quad (7e)$$

Similarly, the problem can be expressed as an unconstrained optimization, $$\min\|\Phi x - y\|_2 + \tau\rho(x) \quad (7f)$$

where r is a regularization parameter or parameters that constrain solutions to match the imposed conditions. A wide range of algorithms are well known to those skilled in the art of solving under-determined linear inverse problems. [13] Most recently sparsity promoting regularization based methods have seen rapid development. [14-17] Other constraints can be used in isolation or in combination with sparsity promoting regularization to refine solutions. For example, the piece-wise continuous nature of the signal both in the spatial and spectral domains enables one to further constrain the problem. This can be done through total variation type approaches that have been demonstrated in the literature. [18-20] Non-negativity constraints fundamentally arise from the multiplexing of illuminants (see equation 6) and the constituents of the basis or dictionary describing the reflectance (see equation 3). These non-negativity constraints can be used to further restrict solutions to the linear inverse problem. [21-23] Incorporating prior knowledge of the optical properties of the scene can lead to further constraints which in turn can lead to useful solutions to equation (7). For example, skin and tissue color occupy a relatively small portion of the RGB color space. Thus, recovered visible light reflected from skin/tissue would be constrained to have RGB values falling within the allowable color space for skin/tissue. Exactly analogous to this, near infrared light reflected from skin and tissue has some general characteristics that can be exploited to limit the range of solutions to the inverse problem. For example, skin/tissue is more highly reflective between 700-800 nm compared to 900-1000 nm. Further constraints that can be employed in tissue imaging include the dramatic differences in the optical properties of tissue in the visible region which is characterized by a high light absorption and the near infrared region in which tissue is weakly absorbing but highly scattering. This prior knowledge of the relative reflectance of tissue across the visible and near infrared spectrum can be incorporated into the optimization problem. Exploiting this prior knowledge effectively means only searching for solutions or accepting solutions to the inverse problem that meet the constraints imposed by this prior knowledge. For example, one example of a physical constraint is that the signals cannot be negative. This means that any negative solutions can immediately be discarded. It may also be known that the lens may transmit different wavelengths of light differently and may result in more blur at longer wavelengths compared to shorter wavelengths, for example. It can be assumed that the signals are piecewise continuous (both spatially and in the wavelength dimension). These types of physical constraints of the imaging system can be used as prior knowledge when processing signals. This can reduce the complexity of solving the inverse problem. In some instances, incorporating both the physical and practical constraints underlying the imaging of a scene can lead to an adequate recovery of the reflectance information from the scene from the measured signal from the sensor. Enforcing the imaging results to conform to the both the underlying physical and practical constraints under which the imaging is performed can lead to greater robustness and reliability. A variation of the above approach which makes maximal use of prior knowledge would be to include a reference material within the scene with known reflectance properties. For example, a material that mimics the reflectance properties of the target could be placed next to the target. The solution which recovers the reflectance information of the reference material could then be applied on the imaging target to recover its reflectance. Equivalently, if the reflectance of portions of the scene are known, a priori, this knowledge can guide the solution of the inverse problem. For example, this prior knowledge could have been obtained from a previous examination or where the optical properties of the target were rigorously measured by spectroscopic methods. As disclosed above, exploiting the optical properties of tissue as well as the practical constraints imposed by the imaging system can lead to an adequate recovery of spectral information from the scene even when the inverse problem of signal recovery is seemingly ill-posed. Such applications can be referred to as sparse frame multi/hyperspectral imaging. As will be illustrated below, such sparse multi/hyperspectral imaging can have particular value when monitoring rapidly changing scenes such as in video frame tissue oxygenated hemoglobin imaging. By being able to capture sufficient spatial and spectral information in a single frame to recovery tissue oxygenation, for example, enables real-time video frame-rate imaging of oxygenation. This can have applications, for example, in measuring the oxygenation of a beating heart without the need for synchronizing the imaging to the heartbeat. The fast multispectral imaging enables the real-time oxygenation imaging of retinal/choroid blood flow as well as the ability to follow the pulsatile modulation of the tissue oxygenation. The latter has applications, for example, in determining arterial sufficiency of the microvascular bed that is being imaged.

The preceding embodiment enabled multi/hyperspectral imaging using a single frame from a CFA RGB sensor often requiring some prior knowledge when the inverse problem is ill-posed to enable joint visible-near infrared multispectral imaging. This prior knowledge can be incorporated as part of the scene being imaged or be based on the physical constraints of the imaging configuration and/or known optical properties of the target being imaged. The embodiment described above can be extrapolated to other encoding schemes, for example, flashing various sequences of light emitting diodes (LED) at the target and using the signals from the R, G, G and B channels to decode the visible and near infrared reflectance from the target. Acquiring further readings of the same scene from the sensor (additional frames) while changing the spectral characteristics of the illuminants enables more robust multi/hyperspectral imaging as well as robust color RGB imaging to be done jointly with near infrared imaging. In one such embodiment, consecutive image frames are acquired with mixed proportions of visible and near infrared illumination. For example, a family of light emitting diodes (LEDs) with different light spectral emission characteristics can be used to change the spectral distribution of the illumination between image frames and thereby enable spectral imaging using these embodiments (see FIG. 7). This could also be done exploiting the method outlined above, incorporating prior knowledge to yield a more robust signal recovery. Increasing the number of sensor frames without changing the overall number of illuminants effectively increases the number of observations. For example, two frames yield 2 k observations where k is the number of channels in the CFA-RGB sensor. With the appropriate initial choice of illuminants relative to the spectral characteristics of the filter channels, as the number of observations approach or exceed the number of illuminants, equation 5 becomes a well posed problem and can be solved in the usual least squares sense to yield robust solutions. Thus, with sufficient frames, the linear inverse problem, visible-near infrared multi/hyperspectral imaging of a scene based on the RGGB sensor output, becomes well posed. This leads to yet another embodiment when visible-near infrared multi/hyperspectral imaging of a scene is done consecutively to, for example, monitor change. In one or more consecutive images of the scene, sufficient frames are acquired to yield a well posed inverse problem yielding robust solutions. Other images of the scene, perhaps consisting of a single frame from the RGGB sensor, result in an under-determined inverse problem. Solutions of the well-posed inverse problem can be used to constrain the solution space of the under-determined inverse problem to provide useful solutions. This procedure has particular utility when following a transient event by taking a series of sparse frame multi/hyperspectral images over the time course of the event. Such a circumstance could arise when following the change in the in-flow of blood during transient ischemia-reperfusion. Such imaging could involve, taking a several frame robust multi/hyperspectral image prior to or after the event, while the event itself can be rapidly imaged using the sparse frame multi/hyperspectral imaging method described in the above paragraphs. By exploiting the prior or post-event multiframe robust multi/hyperspectral image as prior information, the desired information from the ill-posed sparse frame multi/hyperspectral images can be recovered.

According to an aspect of the invention, there is provided a method for visible and/or near-infrared imaging of a sample comprising: subjecting a sample of interest to illumination at an illumination wavelength or an illumination wavelength range by an illuminant, detecting any light reflected by the sample with a color filter array sensor, said color filter array comprising a channel, said channel measuring light intensity at a specific measurement wavelength or a measurement wavelength range as a first channel signal; processing the first channel signal to provide one or more frames of the sample; and assembling the frames into an image of the sample.

As discussed herein, in some embodiments, the color filter array sensor is an RGB sensor, for example an RGB sensor without an IR filter.

According to another aspect of the invention, there is provided a method for visible and/or near-infrared imaging of a sample comprising: subjecting a sample of interest to illumination at a first illumination wavelength or illumination wavelength range by a first illuminant, detecting any light reflected by the sample with a color filter array sensor, said color filter array comprising at least two channels, a first channel measuring light intensity at a first measurement wavelength or measurement wavelength range as a first channel signal and a second channel measuring light intensity at a second measurement wavelength or measurement wavelength range as a second channel signal; processing the first channel signal and the second channel signal to provide frames of the sample; and assembling the frames of the sample into at least one multispectral or hyperspectral image of the sample.

As used herein, a "multispectral image" is an image over two or more wavelengths or wavelength regions. As used herein, a "hyperspectral image" is an image over very many wavelength regions.

According to an aspect of the invention, there is provided a method for visible and/or near-infrared imaging of a sample comprising: subjecting a sample of interest to illumination at an illumination wavelength or an illumination wavelength range by an illuminant, detecting any light reflected by the sample with a color filter array sensor, said color filter array comprising a channel, said channel measuring light intensity at a specific measurement wavelength or a measurement wavelength range as a first channel signal; processing the first channel signal to provide a spectral signal of the sample and comparing the spectral signal of the sample to a library of known spectral signals, thereby identifying the sample.

As discussed herein and as will be apparent to one of skill in the art, in the above embodiment, the abundances are solved directly. That is, by use of a library or database of spectral signatures of samples or compounds of interest, it is possible to solve for the abundances, amounts, and proportions of the components without having to physically assemble the data into a multi/hyperspectral image.

As will be readily apparent to one of skill in the art, this comparison to a library or database may be carried out instead of assembling a multispectral and/or hyperspectral image for identifying components of a sample, as discussed herein.

As will be appreciated by one of skill in the art, in the embodiment described above, there may be more than two channels, for example, 3, 4 or more channels.

The frames may be assembled into more than one image, for example, a color image and a near infrared image. However, regardless of the specific types of images assembled, as a result of the arrangements described herein, the images, for example, the color image and the near infrared image, are spatially aligned. It is important to note that these images are automatically aligned, as discussed herein, and do not require any further manipulation.

According to a further aspect of the invention, there is provided a method for visible and/or near-infrared imaging of a sample comprising: subjecting a sample of interest to illumination at a first illumination wavelength or an illumination wavelength range by a first illuminant, detecting any light reflected by the sample from the first illumination wavelength or illumination wavelength range with a color filter array sensor, said color filter array comprising a first channel and a second channel, said first channel measuring light intensity at a specific measurement wavelength or measurement wavelength range as a first channel signal of the first illumination wavelength; processing the first channel signal of the first illumination wavelength to provide one or more frames at the first illumination wavelength of the sample; subjecting the sample of interest to illumination at a second illumination wavelength or illumination wavelength range by a second illuminant, detecting any light reflected by the sample from the second illumination wavelength or illumination wavelength range with the color filter array sensor, said second channel measuring light intensity as a second channel signal of the second illumination wavelength; processing the second channel signal of the second illumination wavelength to provide one or more frames at the second illumination wavelength of the sample; and assembling the frames into at least one multispectral or hyperspectral image of the sample.

As will be apparent to one of skill in the art, in these embodiments, the sample may be subjected to more than two illuminants. Furthermore, as discussed herein, the sample may be subjected to the illuminants individually or in various combinations.

According to another aspect of the invention, there is provided a method for visible and/or near-infrared imaging of a sample comprising: providing a color filter array comprising a first channel and a second channel, said first channel measuring light intensity at a first measurement wavelength or measurement wavelength range, said second channel measuring light intensity at a second measurement wavelength or measurement wavelength range; subjecting a sample of interest to illumination at a first illumination wavelength by a first illuminant, detecting any light reflected by the sample from the first illumination wavelength or illumination wavelength range with the color filter array sensor, said first channel measuring light intensity as a first channel signal of the first illumination wavelength, said second channel measuring light intensity as a second channel signal of the first illumination wavelength; processing the first channel signal of the first illumination wavelength and the second channel signal of the first illumination wavelength to provide first wavelength frames of the sample; subjecting the sample of interest to illumination at a second illumination wavelength or illumination wavelength range by a second illuminant, detecting any light reflected by the sample from the illumination at the second illumination wavelength or illumination wavelength range with the color filter array sensor, said second channel measuring light intensity as a second channel signal of the second illumination wavelength; processing the second channel signal of the second illumination wavelength to provide one or more frames at the second illumination wavelength of the sample; and assembling the frames of the first illumination wavelength and the frames of the second illumination wavelength into at least one multispectral or hyperspectral image of the sample.

In the embodiment described above, more than two illuminants and more than two channels may be used. Furthermore, the sample may be subjected to the illuminants individually as well as pair-wise or in other combinations, as discussed herein.

According to a still further aspect of the invention, there is provided a method for visible and/or near-infrared imaging of a sample comprising: providing a color filter array comprising at least a first channel and a second channel, said first channel measuring light intensity at a first measurement wavelength or measurement wavelength range, said second channel measuring light intensity at a second measurement wavelength or measurement wavelength range; subjecting a sample of interest to illumination at a first illumination wavelength by a first illuminant and simultaneously to illumination at at least a second illumination wavelength by at least a second illuminant, detecting any light reflected by the sample with the color filter array sensor, said first channel measuring light intensity as a first channel signal, said second channel measuring light intensity as a second channel signal; processing the first channel signal to separate reflectance from the first illuminant and reflectance from the second illuminant to provide a first channel frame of the first illuminant and a first channel frame of the second illuminant; processing the second channel signal to separate reflectance from the first illuminant and reflectance from the second illuminant to provide a second channel frame of the first illuminant and a second channel frame of the second illuminant; and assembling the frames of the first channel and the frames of the second channel into at least one multispectral or hyperspectral image of the sample.

As discussed herein, in those embodiments wherein the sample is subjected to more than one illuminant at a time, the contribution of each illuminant may be unmixed using means described herein to provide the signal at each individual wavelength of illumination.

According to a still further aspect of the invention, there is provided a method for visible and/or near-infrared imaging of a sample comprising: providing a color filter array comprising at least a first channel and a second channel, said first channel measuring light intensity at a first measurement wavelength or measurement wavelength range, said second channel measuring light intensity at a second measurement wavelength or measurement wavelength range; subjecting a sample of interest to illumination at a first illumination wavelength by a first illuminant and simultaneously to illumination at at least a second illumination wavelength by at least a second illuminant, detecting any light reflected by the sample with the color filter array sensor, said first channel measuring light intensity as a first channel signal, said second channel measuring light intensity as a second channel signal; processing the first channel signal to separate reflectance from the first illuminant and reflectance from the second illuminant to provide a first channel spectral signal of the first illuminant and a first channel spectral signal of the second illuminant; processing the second channel signal to separate reflectance from the first illuminant and reflectance from the second illuminant to provide a second channel spectral signal of the first illuminant and a second channel spectral signal of the second illuminant; and comparing the spectral signals of the sample to a library of known spectral signals, thereby identifying the sample.

As will be apparent to one of skill in the art, the spectral signals of the sample and of the library are compared across common measurement wavelengths and/or measurement wavelength ranges.

According to a still further aspect of the invention, there is provided a method for visible and/or near-infrared imaging of a sample comprising: providing a color filter array comprising at least a first channel and a second channel, said first channel measuring light intensity at a first measurement wavelength or measurement wavelength range, said second channel measuring light intensity at a second measurement wavelength or measurement wavelength range; subjecting a sample of interest to illumination at a first illumination wavelength by a first illuminant and simultaneously to illumination at at least a second illumination wavelength or illumination wavelength range by at least a second illuminant at a first time point, detecting any light reflected by the sample with the color filter array sensor, said first channel measuring light intensity as a first channel signal at the first time point, said second channel measuring light intensity as a second channel signal at the first time point; processing the first channel signal to separate reflectance from the first illuminant at the first time point and reflectance from the second illuminant at the first time point to provide a first channel frame of the first illuminant at the first time point and a first channel frame of the second illuminant at the first time point; processing the second channel signal to separate reflectance from the first illuminant at the first time point and reflectance from the second illuminant at the first time point to provide a second channel frame of the first illuminant at the first time point and a second channel frame of the second illuminant at the first time point; assembling the frames of the first channel at the first time point and the frames of the second channel at the first time point into at least one multispectral or hyperspectral image of the sample at the first time point; after an interval, subjecting the sample of interest to illumination at the first illumination wavelength or illumination wavelength range by the first illuminant and simultaneously to illumination at at least the second illumination wavelength or illumination wavelength range by at least the second illuminant at a second time point, detecting any light reflected by the sample with the color filter array sensor, said first channel measuring light intensity as a first channel signal at the second time point, said second channel measuring light intensity as a second channel signal at the second time point; processing the first channel signal to separate reflectance from the first illuminant at the second time point and reflectance from the second illuminant at the second time point to provide a first channel frame of the first illuminant at the second time point and a first channel frame of the second illuminant at the second time point; processing the second channel signal to separate reflectance from the first illuminant at the second time point and reflectance from the second illuminant at the second time point to provide a second channel frame of the first illuminant at the second time point and a second channel frame of the second illuminant at the second time point; assembling the frames of the first channel at the second time point and the frames of the second channel at the second time point into at least one multispectral or hyperspectral image of the sample at the second time point; and comparing the at least one multispectral or hyperspectral image of the sample at the first time point to the at least one multispectral or hyperspectral image of the sample at the second time point.

It is of note that while processing of the first channel signal and the second channel signal are recited sequentially, in most embodiments, the processing of these signals occurs simultaneously.

According to another aspect of the invention, there is provided a method for visible and/or near-infrared imaging of a sample comprising: providing a color filter array comprising a first channel measuring light intensity at a first measurement wavelength or measurement wavelength range, a second channel measuring light intensity at a second measurement wavelength or measurement wavelength range, a third channel measuring light intensity at a third measurement wavelength or measurement wavelength range, and a fourth channel measuring light intensity at a fourth measurement wavelength or measurement wavelength range, subjecting a sample of interest to illumination at a first illumination wavelength by a first illuminant, detecting any light reflected by the sample with the color filter array sensor, said first channel measuring light intensity as a first channel signal of the first illumination wavelength, said second channel measuring light intensity as a second channel signal of the first illumination wavelength; said third channel measuring light intensity as a third channel signal of the first illumination wavelength, said fourth channel measuring light intensity as a fourth channel signal of the first illumination wavelength; processing the first channel signal of the first illumination wavelength, the second channel signal of the first illumination wavelength, the third channel signal of the first illumination wavelength and the fourth channel signal of the first illumination wavelength to provide first illumination wavelength frames of the sample; subjecting the sample of interest to illumination at a second illumination wavelength or illumination wavelength range by a second illuminant, detecting any light reflected from the second illuminant by the sample with the color filter array sensor, said first channel measuring light intensity as a first channel signal of the second illumination wavelength, said second channel measuring light intensity as a second channel signal of the second illumination wavelength; said third channel measuring light intensity as a third channel signal of the second illumination wavelength, said fourth channel measuring light intensity as a fourth channel signal of the second illumination wavelength; processing the first channel signal of the second illumination wavelength, the second channel signal of the second illumination wavelength, the third channel signal of the second illumination wavelength and the fourth channel signal of the second illumination wavelength to provide second illumination wavelength frames of the sample; assembling the frames of the first illumination wavelength and the frames of the second illumination wavelength into at least one multispectral or hyperspectral image of the sample.

As can be seen, in these embodiments, the color filter array is a four channel color filter array, such as for example an RGGB filter. As discussed herein, such color filter arrays are readily available but often include an "IR cut-off filter" which would not be present in the filters of the invention.

According to a further aspect of the invention, there is provided a method for visible and/or near-infrared imaging of a sample comprising: providing a color filter array comprising a first channel measuring light intensity at a first measurement wavelength or measurement wavelength range, a second channel measuring light intensity at a second measurement wavelength or measurement wavelength range; a third channel measuring light intensity at a third measurement wavelength or measurement wavelength range, and a fourth channel measuring light intensity at a fourth measurement wavelength or measurement wavelength range; subjecting a sample of interest to illumination at a first illumination wavelength by a first illuminant and simultaneously to illumination at at least a second illumination wavelength by at least a second illuminant, detecting any light reflected by the sample with the color filter array sensor, said first channel measuring light intensity as a first channel signal, said second channel measuring light intensity as a second channel signal, said third channel measuring light intensity as a third channel signal, and said fourth channel measuring light intensity as a fourth channel signal; processing the first channel signal to separate reflectance from the first illuminant and reflectance from the second illuminant to provide a first channel frame of the first illuminant and a first channel frame of the second illuminant; processing the second channel signal to separate reflectance from the first illuminant and reflectance from the second illuminant to provide a second channel frame of the first illuminant and a second channel frame of the second illuminant; processing the third channel signal to separate reflectance from the first illuminant and reflectance from the second illuminant to provide a third channel frame of the first illuminant and a third channel frame of the second illuminant; processing the fourth channel signal to separate reflectance from the first illuminant and reflectance from the second illuminant to provide a fourth channel frame of the first illuminant and a fourth channel frame of the second illuminant; assembling the frames of the first channel, the frames of the second channel, the frames of the third channel and the frames of the fourth channel into at least one multispectral or hyperspectral image of the sample.

Methods such as this may be used to for example but by no means limited to measure edema, determine fluid balance in tissues of burn patients, measure hemoglobin oxygen saturation, or detect areas of poor oxygenation. It is noted that other suitable uses will be readily apparent to one of skill in the art.

According to another aspect of the invention, there is provided a method for visible and/or near-infrared imaging of a sample comprising: providing an RGB color filter array comprising four channels; subjecting a sample of interest to illumination at a first illumination wavelength by a first illuminant and simultaneously to illumination at at least a second illumination wavelength by at least a second illuminant at a first time point, detecting any light reflected by the sample with the RGB color filter array sensor, said first channel measuring light intensity as a first channel signal at the first time point, said second channel measuring light intensity as a second channel signal at the first time point, said third channel measuring light intensity as a third channel signal at the first time point, and said fourth channel measuring light intensity as a fourth channel signal at the first time point; processing the first channel signal to separate reflectance from the first illuminant at the first time point and reflectance from the second illuminant at the first time point to provide a first channel frame of the first illuminant at the first time point and a first channel frame of the second illuminant at the first time point; processing the second channel signal to separate reflectance from the first illuminant at the first time point and reflectance from the second illuminant at the first time point to provide a second channel frame of the first illuminant at the first time point and a second channel frame of the second illuminant at the first time point; processing the third channel signal to separate reflectance from the first illuminant at the first time point and reflectance from the second illuminant at the first time point to provide a third channel frame of the first illuminant at the first time point and a third channel frame of the second illuminant at the first time point; processing the fourth channel signal to separate reflectance from the first illuminant at the first time point and reflectance from the second illuminant at the first time point to provide a fourth channel frame of the first illuminant at the first time point and a fourth channel frame of the second illuminant at the first time point; assembling the frames of the first channel at the first time point, the frames of the second channel at the first time point, the frames of the third channel at the first time point and the frames of the fourth channel at the first time point into at least one multispectral or hyperspectral image of the sample at the first time point; after an interval, subjecting the sample of interest to illumination at the first illumination wavelength by the first illuminant and simultaneously to illumination at at least the second illumination wavelength by at least the second illuminant at a second time point, detecting any light reflected by the sample with the RGB color filter array sensor, said first channel measuring light intensity as a first channel signal at the second time point, said second channel measuring light intensity as a second channel signal at the second time point, said third channel measuring light intensity as a third channel signal at the second time point, and said fourth channel measuring light intensity as a fourth channel signal at the second time point; processing the first channel signal to separate reflectance from the first illuminant at the second time point and reflectance from the second illuminant at the second time point to provide a first channel frame of the first illuminant at the second time point and a first channel frame of the second illuminant at the second time point; processing the second channel signal to separate reflectance from the first illuminant at the second time point and reflectance from the second illuminant at the second time point to provide a second channel frame of the first illuminant at the second time point and a second channel frame of the second illuminant at the second time point; processing the third channel signal to separate reflectance from the first illuminant at the second time point and reflectance from the second illuminant at the second time point to provide a third channel frame of the first illuminant at the second time point and a third channel frame of the second illuminant at the second time point; processing the fourth channel signal to separate reflectance from the first illuminant at the second time point and reflectance from the second illuminant at the second time point to provide a fourth channel frame of the first illuminant at the second time point and a fourth channel frame of the second illuminant at the second time point; assembling the frames of the first channel at the second time point, the frames of the second channel at the second time point, the frames of the third channel at the second time point and the frames of the fourth channel at the second time point into at least one multispectral or hyperspectral image of the sample at the first time point; comparing the at least one multispectral or hyperspectral image of the sample at the first time point to the at least one multispectral or hyperspectral image of the sample at the second time point.

As will be readily apparent to one of skill in the art and as discussed herein, methods such as this can be used to monitor changes over time. Specifically, these methods may be used to monitor changes over time, for example, but by no means limited to, monitoring edema of fluid balance in tissues of for example burn patients, or measuring changes in hemoglobin oxygen saturation, for example, video frame tissue oxygenated hemoglobin imaging. The methods may also be used to image blood flow, for example, retinal/choroid blood flow or the in-flow of blood during transient ischemia-reperfusion, or to measure oxygenation of a beating heart (without needing to synchronize the image to the heart beat), or to follow the pulsatile modulation of tissue oxygenation such as for example determining the arterial sufficiency of the microvascular bed.

As discussed above, accuracy or "robustness" of measurements may be improved by using standards or a dictionary as discussed herein as well as by taking into account previously known characteristics of the sample as well as physical constraints associated with imaging of the sample, as discussed herein.

In summary, one illuminant taken with one frame of the sensor gives you a regular black and white picture. Changing illuminants and taking a frame with each different illuminant results in multispectral/hyperspectral imaging. The CFA-RGB sensor is a multi-channel sensor that has 4 channels. Although those channels are designed to detect red, green or blue light, they can also detect near infrared light. In most uses of RGB sensors, this sensitivity to near infrared light is ignored and often blocked. As shown in FIG. 5c, the R, G, and B channels each have a different sensitivity to NIR light. The blue channel has almost zero sensitivity to light between 650-750 nm, while the green channel has intermediate sensitivity over that same wavelength range and red is very sensitivity in that range. The R, G, and B channels have almost the same sensitivity between 850 to 1000 nm. Thus using an illuminant at 900 nm will give the same result from all 4 channels (RGGB); however, an illuminant at 650 will only give a high signal on the red channel. By exploiting the varying sensitivities of the RGGB channels over the NIR, we can "unmix" the NIR illuminants. As discussed herein, this feature is used to do visible-near infrared hybrid imaging with a single sensor. By choosing our illuminant wavelengths appropriately we can easily unmix the reflectance from a combination of up to 4 illuminants with a single frame of the sensor because we have 4 channels. Basically with 4 unknowns (reflectance from illuminants) but 4 equations (channels), we can solve for the illuminant reflectance. When there are more unknowns/illuminants than equations/channels, one solution to this is acquire multiple frames with a different set of illuminants for each frame. Thus for each frame we have enough equations to solve for the unknowns (each frame acquired with a combination of 4 or fewer illuminants). Alternatively, if there are more than 4 illuminants combined in a frame (more unknowns/illuminants than equations/channels), there are mathematical techniques to solve these "under determined" systems.

Figure 7:
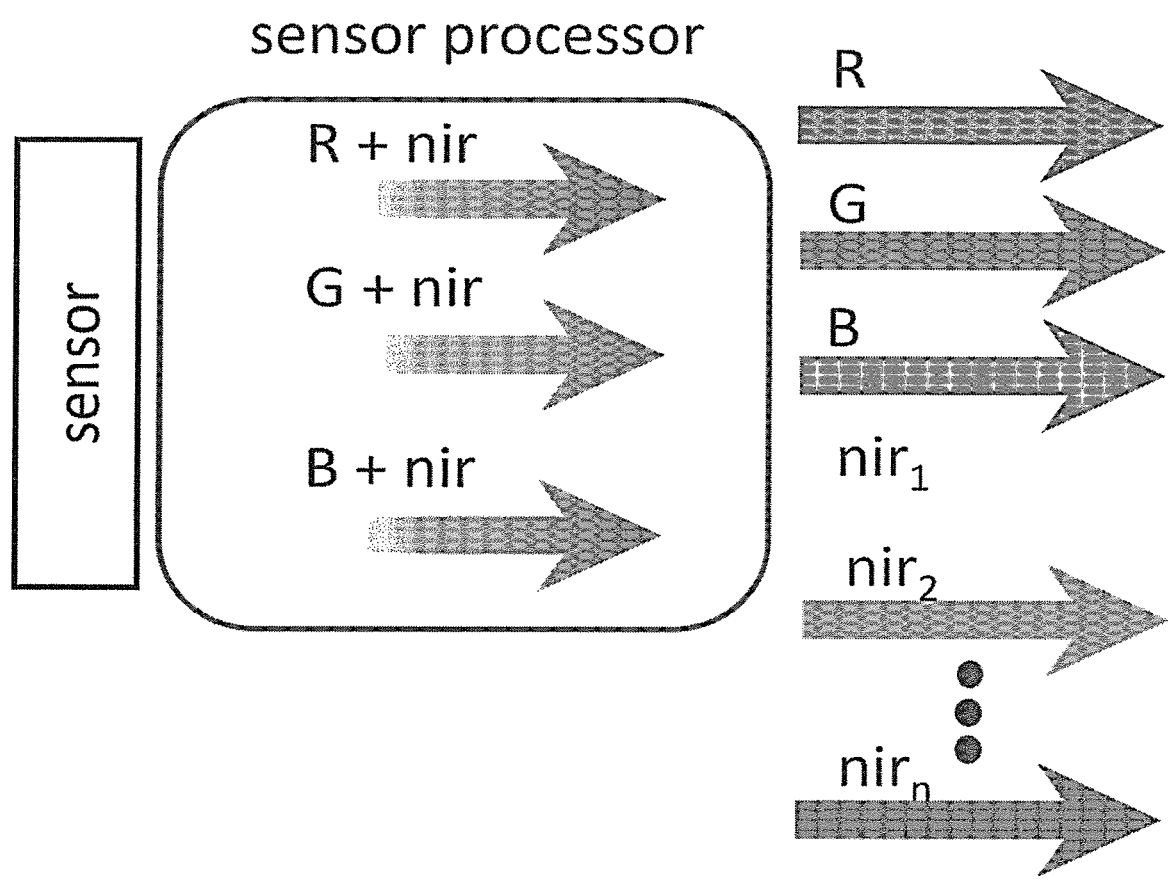
FIG. 7: A scene illuminated by a broadband visible light source and nir light sources is captured by a RGGB sensor. The R+nir, G+nir and B+nir signals from the sensor are unmixed using one or more of the embodiments described herein to provide R, G, B color and multiple nir signals to enable multispectral or hyperspectral near infrared imaging.

The general descriptions provided above also lend themselves to some simple practice. The simplest way to perform multispectral and hyperspectral near infrared image in conjunction with color imaging is to acquire a series of consecutive frames under different near infrared spectral lighting conditions. For example, the separated R, G and B components of the signal make up the color image while the separated near infrared response provides for the near infrared image. In this manner, the final color and near infrared image are provided without out-of-band spectral contamination. For example we could acquire two consecutive frames without visible light illumination but with one of the frames a null image, that is, taken under ambient tight and the second one of the frames having near infrared illumination. Subtracting the ambient light-level frame from the frame where the scene is illuminated with near infrared light results in a near infrared image without visible light contamination. As will be appreciated by one of skill in the art, any specific wavelength, for example, NIR or visible, or any range of wavelengths, for example, a white-light LED, may be used. In this mode of operation, near infrared imaging is largely immune to the ambient light level under which imaging is carried out. Following this approach but only using visible light to illuminate one of the two consecutive frames one can obtain an RGB image without contamination from the near infrared response of the sensor. The above practice works when the proportion of visible and near infrared light reaching the sensor is unknown but where one of the components remains fixed between the two consecutive images. Subtraction of the consecutive images eliminates the fixed proportion of illumination between the two frames. This example is one form of binary encoding; however, other methods for combining these methods are also feasible and will be readily apparent to one of skill in the art. FIGS. 6 and 7 show embodiments where broadband white length, for example a white-light LED, is separated from a near infrared illumination source(s) using approaches disclosed herein.

We have outlined several strategies by which one color filter array RGB sensor can be used to hybrid visible and near infrared imaging. In one such strategy several consecutive frames are acquired from the sensor and processed to provide an RGB color image and near infrared image(s) or a hyper/multispectral visible, near infrared or visible-near infrared image. Further strategies were introduced to reduce the number of frames needed to recovery the visible-near infrared reflectance information from the scene being imaged. At the limit when the measured signals from the sensor under-determine the desired information from the scene, prior knowledge of the optical properties of the scene and the physical constraints imposed by the imaging configuration can be used to recover the required information from the scene.

The scope of the claims should not be limited by the preferred embodiments set forth in the examples but should be given the broadest interpretation consistent with the description as a whole.

REFERENCES

1. Michael G. Sowa, Wen-Chuan Kuo, Alex C-T. Ko, David G. Armstrong, "Review of near-infrared methods for wound assessment," J. Biomed. Opt. 21 (9), 091304 (2016), doi: 10.1117/1.JBO.21.9.091304.
2. Michael Sowa, Jeri Friesen, Michelle Levasseur, Bernhard Schattka, Leif Sigurdson, Thomas Hayakawa: The utility of near infrared imaging in intra-operative prediction of flap outcome: a reverse McFarlane skin flap model study. Journal of Near Infrared Spectroscopy January 2012; 20(5): 601-. DOI: 10.1255/jnirs. 1007
3. Michael G Sowa-, Lorenzo Leonardi, Jeri R Payette, Karen M Cross, Manuel Gomez, Joel S Fish: Classification of burn injuries using near-infrared spectroscopy. . . . Journal of Biomedical Optics January 2006; 11(5): 054002. DOI: 10.1117/1.2362722
4. Michael Sowa, Elicia Kohlenberg, Jeri Payette, Lorenzo Leonardi, Michelle Levasseur, Christopher Riley: Detecting intestinal ischemia using near infrared spectroscopy. Journal of Near Infrared Spectroscopy January 2006; DOI: 10.1255/jnirs.580
5. Xiaoming Xiang, Michael G Sowa, Anthony M Iacopino, Roman G Maev, Mark D Hewko, Angela Man, Kan-Zhi Liu: An update on novel non-invasive approaches for periodontal diagnosis . . . Journal of Periodontology February 2010; 81(2):186-98. DOI:10.1902/jop.2009.090419
6. Michael Attas, Mark Hewko, Jeri Payette, Trevor Posthumus, Michael Sowa, Henry Mantsch: Visualization of cutaneous hemoglobin oxygenation and skin hydration using near-infrared spectroscopic imaging. Skin Research and Technology December 2001; 7(4):238-45. DOI: 10.1034/j.1600-0846.2001.70406.x
7. Pierre-Jean Lapray, Xingbo Wang, Jean-Baptiste Thomas and Pierre Gouton, Multispectral Filter Arrays: Recent Advances and Practical Implementation. Sensors 2014, 14(11), 21626-21659
8. Hannah R. Morris, Clifford C. Hoyt, and Patrick J. Treado, "Imaging Spectrometers for Fluorescence and Raman Microscopy: Acousto-Optic and Liquid Crystal Tunable Filters," Appl. Spectrosc. 48, 857-866 (1994).
9. R. Lukac and K. N. Plataniotis, "Color filter arrays: design and performance analysis," in IEEE Transactions on Consumer Electronics, vol. 51, no. 4, pp. 1260-1267 November 2005.
10. R. Heylen, M. Parente and P. Gader, "A Review of Nonlinear Hyperspectral Unmixing Methods," in IEEE Journal of Selected Topics in Applied Earth Observations and Remote Sensing, vol. 7, no. 6, pp. 1844-1868 June 2014.
11. N. Dobigeon, J. Y. Tourneret, C. Richard, J. C. M. Bermudez, S. McLaughlin and A. 0. Hero, "Nonlinear Unmixing of Hyperspectral Images: Models and Algorithms," in IEEE Signal Processing Magazine, vol. 31, no. 1, pp. 82-94, January 2014.
12. H. Pu, Z. Chen, B. Wang and W. Xia, "Constrained Least Squares Algorithms for Nonlinear Unmixing of Hyperspectral Imagery," in IEEE Transactions on Geoscience and Remote Sensing, vol. 53, no. 3, pp. 1287-133 March 2015.
13. Chandrasekaran, V., Recht, B., Parrilo, P. A. et al. Found Comput Math (2012) 12: 805.
14. D. Tuia, R. Flamary and M. Barlaud, "Nonconvex Regularization in Remote Sensing," in IEEE Transactions on Geoscience and Remote Sensing, vol. 54, no. 11, pp. 6470-6480 November 2016.
15. J. A. Tropp and S. J. Wright, "Computational Methods for Sparse Solution of Linear Inverse Problems," in Proceedings of the IEEE, vol. 98, no. 6, pp. 948-958, June 2010.
16. Amir Beck and Marc Teboulle, A Fast Iterative Shrinkage-Thresholding Algorithm for Linear Inverse Problems, SIAM Journal on Imaging Sciences 2009 2:1, 183-202.
17. S. F. Cotter, B. D. Rao, Kjersti Engan and K. Kreutz-Delgado, "Sparse solutions to linear inverse problems with multiple measurement vectors," in IEEE Transactions on Signal Processing, vol. 53, no. 7, pp. 2477-2488 July 2005.
18. Y. E. Salehani, S. Gazor, 1-M Kim and S Yousefi, "to-Norm Sparse Hyperspectral Unmixing Using Arctan Smoothing", Remote Sens. 2016, 8 (3), 187.
19. M. D. Iordache, J. M. Bioucas-Dias and A. Plaza, "Total Variation Spatial Regularization for Sparse Hyperspectral Unmixing," in IEEE Transactions on Geoscience and Remote Sensing, vol. 50, no. 11, pp. 4484-452 November 2012.
20. Q. Yuan, L. Zhang and H. Shen, "Hyperspectral Image Denoising Employing a Spectral-Spatial Adaptive Total Variation Model," in IEEE Transactions on Geoscience and Remote Sensing, vol. 50, no. 10, pp. 3660-3677 October 2012.
21. David L. Donoho and Jared Tanner, Sparse nonnegative solution of underdetermined linear equations by linear programming PNAS 2005 102 (27) 9446-9451.
22. A. M. Bruckstein, M. Elad and M. Zibulevsky, "On the Uniqueness of Nonnegative Sparse Solutions to Underdetermined Systems of Equations," in IEEE Transactions on Information Theory, vol. 54, no. 11, pp. 4813-4820 November 2008.
23. M. Wang, W. Xu and A. Tang, "A Unique "Nonnegative" Solution to an Underdetermined System: From Vectors to Matrices," in IEEE Transactions on Signal Processing, vol. 59, no. 3, pp. 1007-116 March 2011.

What is claimed is:
1. A system configured to image a sample of interest, comprising:
a first illuminant source configured to illuminate the sample of interest, wherein the first illuminant source is configured to emit at a first illuminant wavelength;
a second illuminant source configured to illuminate the sample of interest, wherein the second illuminant source is configured to emit a second illuminant wavelength; and
an image sensor comprising a first channel and a second channel, wherein the system is configured to:
measure a first reflected light intensity of the first illuminant wavelength;
measure a second reflected light intensity of the second illuminant wavelength;
produce, by mathematical unmixing, a first illuminant wavelength first channel signal from the first channel in response to the first reflected light intensity and a second illuminant wavelength first channel signal from the first channel in response to the second reflected light intensity;
produce, by mathematical unmixing, a first illuminant wavelength second channel signal from the second channel response to the first reflected light intensity and a second illuminant wavelength second channel signal from the second channel in response to the second reflected light intensity;
generate one or more first illumination image frames from the first illuminant wavelength first channel signal and the first illuminant wavelength second channel signal, wherein the first illumination image frames indicate hemoglobin oxygen saturation;
generate one or more second illumination image frames from the second illuminant wavelength first channel signal and the second illuminant wavelength second channel signal, wherein the second illumination image frames indicate hemoglobin oxygen saturation; and
assemble the one or more first illumination image frames and the one or more second illumination image frames to generate at least one multispectral or hyperspectral image of the hemoglobin oxygen saturation of the sample of interest.

2. The system of claim 1, wherein the system is further operable to:
separately produce the first illuminant wavelength first channel signal representing the collected light of the first illuminant wavelength.

3. The system of claim 1, wherein the system is further operable to:
separately produce the first illuminant wavelength second channel signal representing the collected light of the first illuminant wavelength in the second channel.

4. The system of claim 1, wherein the system is further operable to:
separately produce the second illuminant wavelength first channel signal representing the collected light of the second illuminant wavelength in the first channel.

5. The system of claim 1, wherein the system is further operable to:
separately produce a second illuminant wavelength second channel signal representing the collected light of the second illuminant wavelength in the second channel.

6. The system of claim 1, wherein the image sensor is an RGB sensor without an IR filter.

7. The system of claim 1, wherein the first illuminant wavelength and the second illuminant wavelength comprise light from 350 nm to 1100 nm.

8. The system of claim 1, wherein the first illuminant source and the second illuminant source are configured to emit visible light.

9. The system of claim 1, wherein the first illuminant source and the second illuminant source are configured to emit near-infrared light.

10. The system of claim 1, wherein the system, when assembling the first illumination image frames and the second illumination image frames, is further operable to:
assemble the first illumination image frames into a color image of the sample; and
assemble the second illumination image frames into a near infrared image of the sample.

11. The system of claim 10, wherein the color image and the near infrared image are automatically spatially aligned.

12. A method for visible and/or near-infrared imaging of a sample of interest, comprising:
measuring a first reflected light intensity of a first illuminant wavelength emitted by a first illuminant source;
measuring a second reflected light intensity of a second illuminant wavelength emitted by a second illuminant source;
generating, by mathematical unmixing, a first illuminant wavelength first channel signal from a first channel of an image sensor in response to the first reflected light intensity and a second illuminant wavelength first channel signal from the first channel in response to the second reflected light intensity;
generating, by mathematical unmixing, a first illuminant wavelength second channel signal from the second channel of an image sensor upon receiving the first reflected light intensity and a second illuminant wavelength second channel signal from the second channel upon receiving the second reflected light intensity;
generating one or more first illumination image frames from the first illuminant wavelength first channel signal and the first illuminant wavelength second channel signal, wherein the first illumination image frames indicate hemoglobin oxygen saturation;
generating one or more second illumination image frames from the second illuminant wavelength first channel signal and the second illuminant wavelength second channel signal, wherein the second illumination image frames indicate hemoglobin oxygen saturation; and
generating at least one multispectral image of the hemoglobin oxygen saturation by assembling the first illumination image frames and the second illumination image frames.

13. The method of claim 12, wherein the first illuminant wavelength first channel signal represents the collected light of the first reflected light intensity of the first illuminant wavelength by the first channel and is produced separately from the first illuminant wavelength second channel signal.

14. The method of claim 12, wherein the first illuminant wavelength second channel signal represents the collected light of the first reflected light intensity of the first illuminant wavelength by the second channel and is produced separately from the first illuminant wavelength first channel signal.

15. The method of claim 12, wherein the second illuminant wavelength first channel signal represents the collected light of the second reflected light intensity of the second illuminant wavelength and is produced separately from the second illuminant wavelength second channel signal.

16. The method of claim 12, wherein the second illuminant wavelength second channel signal represents the collected light of the second reflected light intensity of the second illuminant wavelength and is produced separately from the second illuminant wavelength first channel signal.

17. The method of claim 12, wherein the image sensor is an RGB sensor without an IR filter.

18. The method of claim 12, wherein the first illuminant wavelength and the second illuminant wavelength comprise light from 350 nm to 1100 nm.

19. The method of claim 12, further comprising:
illuminating the sample of interest with a first illuminant source that emits visible light.

20. The method of claim 12, further comprising:
illuminating the sample of interest with a second illuminant source that emits near-infrared light.

21. The method of claim 12, further comprising:
assembling the first illumination image frames into a color image of the sample; and
assembling the second illumination image frames into a near infrared image of the sample.

22. The method of claim 12, further comprising:
automatically spatially aligning the color image and the near infrared image.

* * * * *